US007907701B2

(12) United States Patent
Anderson (10) Patent No.: US 7,907,701 B2
(45) Date of Patent: *Mar. 15, 2011

(54) ELECTROMAGNETIC COIL ARRAY INTEGRATED INTO ANTISCATTER GRID

(75) Inventor: Peter Traneus Anderson, Andover, MA (US)

(73) Assignee: General Electric Company, Schenectady, NY (US)

(*) Notice: Subject to any disclaimer, the term of this patent is extended or adjusted under 35 U.S.C. 154(b) by 1476 days.

This patent is subject to a terminal disclaimer.

(21) Appl. No.: 11/322,416

(22) Filed: Dec. 30, 2005

(65) Prior Publication Data

US 2006/0154604 A1    Jul. 13, 2006

Related U.S. Application Data

(63) Continuation-in-part of application No. 10/611,112, filed on Jul. 1, 2003, now Pat. No. 7,158,754.

(51) Int. Cl.
*G21K 1/00* (2006.01)
(52) U.S. Cl. .......................................... 378/154; 378/155
(58) Field of Classification Search .................. 378/154, 378/155, 98, 8; 250/370.09
See application file for complete search history.

(56) References Cited

U.S. PATENT DOCUMENTS

| 6,445,943 | B1 | 9/2002 | Ferre et al. |
| 6,484,049 | B1 | 11/2002 | Seeley et al. |
| 6,490,475 | B1 | 12/2002 | Seeley et al. |
| 6,636,757 | B1 | 10/2003 | Jascob et al. |
| 6,774,624 | B2 | 8/2004 | Anderson et al. |
| 6,856,826 | B2 | 2/2005 | Seeley et al. |
| 6,856,827 | B2 | 2/2005 | Seeley et al. |
| 7,580,676 | B2 * | 8/2009 | Anderson .................... 455/41.1 |
| 2002/0113747 | A1 * | 8/2002 | Tessier et al. ................. 343/787 |

* cited by examiner

*Primary Examiner* — Irakli Kiknadze
(74) *Attorney, Agent, or Firm* — McAndrews, Held & Malloy, Ltd.; Michael A. Dellapenna (57) ABSTRACT

Certain embodiments of the present invention provide an antiscatter grid including an electromagnetic coil array integrated with the antiscatter grid. The electromagnetic coil array is registered with the antiscatter grid. The electromagnetic coil array is configured to detect an electromagnetic field at the antiscatter grid. In an embodiment, the electromagnetic coil array may be positioned in front of the antiscatter grid. In an embodiment, the electromagnetic coil array may be positioned behind the antiscatter grid. In an embodiment, the electromagnetic coil array may be attached to the antiscatter grid. In an embodiment, a portion of the electromagnetic coil array may be transparent to x-rays. In an embodiment, the electromagnetic coil array may include one or more electromagnetic coils. In an embodiment, the electromagnetic coil array may be a printed circuit board (PCB) electromagnetic coil array.

26 Claims, 9 Drawing Sheets

ELECTROMAGNETIC COIL ARRAY INTEGRATED INTO ANTISCATTER GRID

RELATED APPLICATIONS

This application is a continuation-in-part of U.S. patent application Ser. No. 10/611,112 filed Jul. 1, 2003 now U.S. Pat. No. 7,158,754, which is herein incorporated by reference.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to an electromagnetic tracking system. In particular, the present invention relates to an electromagnetic tracking system with an electromagnetic coil array integrated into an antiscatter grid.

Many medical procedures involve a medical instrument, such as a drill, a catheter, scalpel, scope, stent or other tool. In some cases, a medical imaging or video system may be used to provide positioning information for the instrument, as well as visualization of an interior of a patient. However, medical practitioners often do not have the use of medical imaging systems when performing medical procedures. Typically, medical imaging systems are too slow to produce useable real-time images for instrument tracking in medical procedures. The use of medical imaging systems for instrument tracking may be also limited for health and safety reasons (e.g., radiation dosage concerns), financial limitations, physical space restrictions, and other concerns, for example.

Medical practitioners, such as doctors, surgeons, and other medical professionals, often rely upon technology when performing a medical procedure, such as image-guided surgery or examination. A tracking system may provide positioning information of the medical instrument with respect to the patient or a reference coordinate system, for example. A medical practitioner may refer to the tracking system to ascertain the position of the medical instrument when the instrument is not within the practitioner's line of sight. A tracking system may also aid in presurgical planning.

The tracking or navigation system allows the medical practitioner to visualize the patient's anatomy and track the position and orientation of the instrument. The medical practitioner may use the tracking system to determine when the instrument is positioned in a desired location. The medical practitioner may locate and operate on a desired or injured area while avoiding other structures. Increased precision in locating medical instruments within a patient may provide for a less invasive medical procedure by facilitating improved control over smaller instruments having less impact on the patient. Improved control and precision with smaller, more refined instruments may also reduce risks associated with more invasive procedures such as open surgery.

Tracking systems may also be used to track the position of items other than medical instruments in a variety of applications. That is, a tracking system may be used in other settings where the position of an instrument in an object or an environment is unable to be accurately determined by visual inspection. For example, tracking technology may be used in forensic or security applications. Retail stores may use tracking technology to prevent theft of merchandise. In such cases, a passive transponder may be located on the merchandise. A transmitter may be strategically located within the retail facility. The transmitter emits an excitation signal at a frequency that is designed to produce a response from a transponder. When merchandise carrying a transponder is located within the transmission range of the transmitter, the transponder produces a response signal that is detected by a receiver. The receiver then determines the location of the transponder based upon characteristics of the response signal.

Tracking systems are also often used in virtual reality systems or simulators. Tracking systems may be used to monitor the position of a person in a simulated environment. A transponder or transponders may be located on a person or object. A transmitter emits an excitation signal and a transponder produces a response signal. The response signal is detected by a receiver. The signal emitted by the transponder may then be used to monitor the position of a person or object in a simulated environment.

Tracking systems may be ultrasound, inertial position, or electromagnetic tracking systems, for example. Electromagnetic tracking systems may employ coils as receivers and transmitters. Typically, an electromagnetic tracking system is configured in an industry-standard coil architecture (ISCA). ISCA uses three colocated orthogonal quasi-dipole transmitter coils and three colocated quasi-dipole receiver coils. Other systems may use three large, non-dipole, non-colocated transmitter coils with three colocated quasi-dipole receiver coils. Another tracking system architecture uses an array of six or more transmitter coils spread out in space and one or more quasi-dipole receiver coils. Alternatively, a single quasi-dipole transmitter coil may be used with an array of six or more receivers spread out in space.

The ISCA tracker architecture uses a three-axis quasi-dipole coil transmitter and a three-axis quasi-dipole coil receiver. Each three-axis transmitter or receiver is built so that the three coils exhibit the same effective area, are oriented orthogonal to one another, and are centered at the same point. The exact sizes, shapes, and relative-to-one-another positions of the transmitter and receiver coil-trios are measured in manufacturing. If the coils are small enough compared to a distance between the transmitter and receiver, then the coil may exhibit dipole behavior. Magnetic fields generated by the trio of transmitter coils may be detected by the trio of receiver coils. Nine transmitter-receiver mutual inductance measurements may be obtained. From these nine parameter measurements and the information determined in manufacturing, a position and orientation determination of the receiver coil-trio may be made with respect to the transmitter coil-trio for all six degrees of freedom.

Some existing electromagnetic tracking systems include a transmitter and receiver wired to a common device or box. In system with the transmitter and receiver wired to a common device, the object being tracked is wired to the same device as the components performing the tracking. Thus, the range of motion of the object being tracked is limited.

Wireless electromagnetic tracking systems allow for the object being tracked to move freely without being limited by connections with the transmitter or receiver. To reduce the bulk associated with attaching a battery or other power source to a transponder, passive transponders may employ a coil as a means of coupling with and receiving power from other devices.

Typically, a transponder is located on or within a device in order to track movement of the device. In order to determine the transponder's location, a transmitter generates an excitation signal that is incident on the transponder. The incidence of the excitation signal on the transponder causes the transponder to emit a response signal. Typically, the response signal is emitted at the same frequency as the excitation signal.

The response signal emitted by the transponder and the excitation signal emitted by the transmitter are incident upon a receiving coil. Typically, in a tracking system using a passive transponder the excitation signal is much larger than the response signal when both signals are received at the receiver. Because the response signal is emitted at the same frequency as the excitation signal and the response signal is much smaller than the excitation signal, accurately separating and measuring the response signal is difficult.

When using an electromagnetic tracking system to track the position and orientation of an x-ray detector in a fluoroscope, for example, an electromagnetic coil array (transmitter or receiver) is typically mounted on the detector assembly. More particularly, the electromagnetic coil array is typically mounted on the outside of the detector assembly. For example, Anderson et al. (U.S. Pat. No. 6,774,624), Seeley et al. (U.S. Pat. Nos. 6,484,049, 6,490,475, 6,856,826 and 6,856,827), Ferre et al. (U.S. Pat. No. 6,445,943), and Jascob et al. (U.S. Pat. No. 6,636,757) disclose electromagnetic coil arrays mounted on the outside of the detector assembly. In particular, Jascob et al. (U.S. Pat. No. 6,636,757) provides that "offsetting the set of transmitting coils 62 from the shield 54 creates less inteference or cancelling of the electromagnetic field because of the shield 54, to provide enhanced performance." Additionally, Ferre et al. provides that "since the presence of magnetic material might interfere with the magnetic fields these materials are to be avoided in such an electromagnetic system."

Furthermore, modern x-ray detectors, such as amorphous silicon flat-panel x-ray detectors, typically do not include enough space for mounting an electromagnetic coil array on the inside of the detector assembly (where the electromagnetic coil array would be in the field of view of the detector, and thus, most effective). As such, current electromagnetic coil arrays typically include a small coverage area and are offset from the detector. Consequently, the patient or detector (including the electromagnetic coil array) must be repositioned several times, thereby inconveniencing the patient and wasting valuable time, money, and other valuable resources.

Thus, a need exists for an electromagnetic coil array in the field of view of an x-ray detector. More particularly, a need exists for an electromagnetic coil array integrated into an antiscatter grid.

BRIEF SUMMARY OF THE INVENTION

Certain embodiments of the present invention provide an antiscatter grid including an electromagnetic coil array integrated with the antiscatter grid. The electromagnetic coil array is registered with the antiscatter grid. The electromagnetic coil array is configured to detect an electromagnetic field at the antiscatter grid. In an embodiment, the electromagnetic coil array may be positioned in front of the antiscatter grid. In an embodiment, the electromagnetic coil array may be positioned behind the antiscatter grid. In an embodiment, the electromagnetic coil array may be attached to the antiscatter grid. In an embodiment, a portion of the electromagnetic coil array may be transparent to x-rays. In an embodiment, the electromagnetic coil array may be a printed circuit board (PCB) electromagnetic coil array. In an embodiment, the PCB electromagnetic coil array may include one or more electromagnetic coils. In an embodiment, the PCB electromagnetic coil array may include a substrate. The substrate may be transparent to x-rays. In an embodiment, the electromagnetic coil array may be an electromagnetic receiver. In an embodiment, the electromagnetic coil array may be an electromagnetic transmitter. In an embodiment, the electromagnetic coil array may be an electromagnetic transceiver. In an embodiment, the electromagnetic coil array may include one or more electromagnetic coils.

Certain embodiments of the present invention provide a method for detecting an electromagnetic field with an antiscatter grid. The method includes integrating an electromagnetic coil array with an antiscatter grid. The method also includes detecting the electromagnetic field at the antiscatter grid with the integrated electromagnetic coil array. The electromagnetic coil array is registered with the antiscatter grid. In an embodiment, the electromagnetic coil array may be positioned in the field of view of the antiscatter grid. In an embodiment, the electromagnetic coil array may be a printed circuit board (PCB) electromagnetic coil array. In an embodiment, the PCB electromagnetic coil array may include one or more electromagnetic coils. In an embodiment, the electromagnetic coil array may be an electromagnetic receiver. In an embodiment, the electromagnetic coil array may be an electromagnetic transceiver.

Certain embodiments of the present invention provide a method for using an electromagnetic coil array as an antiscatter grid. The method includes providing the electromagnetic coil array. The method also includes filtering scattered x-rays with the electromagnetic coil array. In an embodiment, the electromagnetic coil array may be a printed circuit board (PCB) electromagnetic coil array. The PCB electromagnetic coil array may include a substrate and one or more tracks. The substrate may be transparent to x-rays. The tracks may be opaque to x-rays.

Certain embodiments of the present invention provide a method for registering an electromagnetic coil array with an antiscatter grid. The method includes positioning the antiscatter grid and the electromagnetic coil array in an imaging system, acquiring an image of the antiscatter grid and the electromagnetic coil array, and determining that the electromagnetic coil array is registered with the antiscatter grid based at least in part on the acquired image. In an embodiment, the determining step may be based at least in part on the presence of a moire pattern in the acquired image. In an embodiment, the determining step may be based at least in part on the visibility of the electromagnetic coil array. In an embodiment, the method also may include repositioning the antiscatter grid and the electromagnetic coil array in the imaging system.

Certain embodiments of the present invention provide a printed circuit board (PCB) electromagnetic coil array integrated with an antiscatter grid, the PCB electromagnetic coil array configured to detect an electromagnetic field at the antiscatter grid.

Certain embodiments of the present invention provide a printed circuit board (PCB) electromagnetic coil array configured to function as an antiscatter grid.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 1:
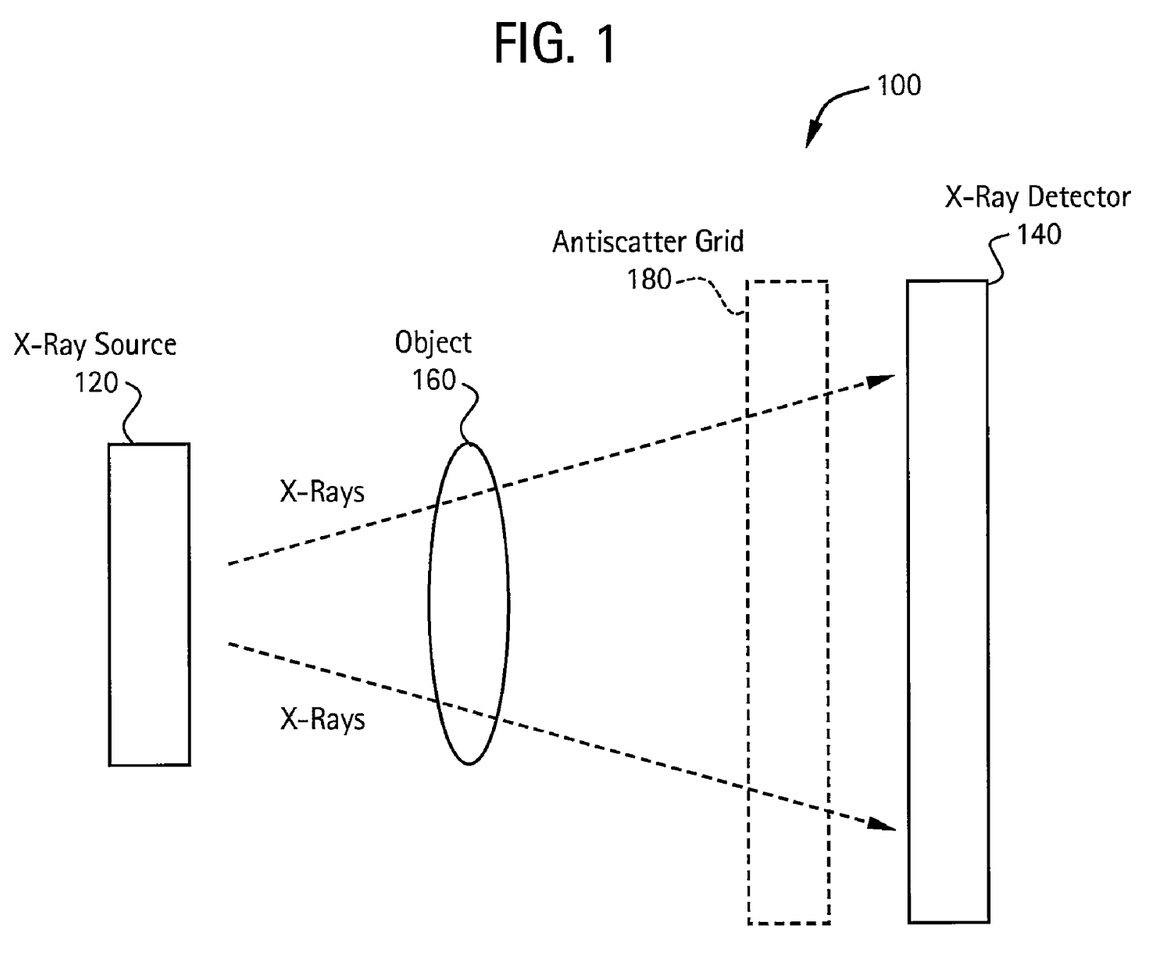
FIG. 1 illustrates an imaging system in accordance with an embodiment of the present invention.

FIG. 1 illustrates an imaging system 100 in accordance with an embodiment of the present invention. For purposes of illustration only, the imaging system 100 is described as an x-ray imaging system. As appreciated by one of ordinary skill in the art, other imaging systems may be similarly implemented. The imaging system 100 includes an x-ray source 120 and an x-ray detector 140. An object 160 may also be present in the imaging system 100.

In an embodiment, the object 160 may be positioned between the x-ray source 120 and the x-ray detector 140. The x-ray source 120 may transmit x-rays to the object 160. The x-ray detector 140 may receive x-rays from the object 160. In other words, the x-rays may travel from the x-ray source 120, through the object 160, and to the x-ray detector 140. As appreciated by one of ordinary skill in the art, the x-rays received by the x-ray detector 140 may represent the structure of the object 160.

Figure 3:
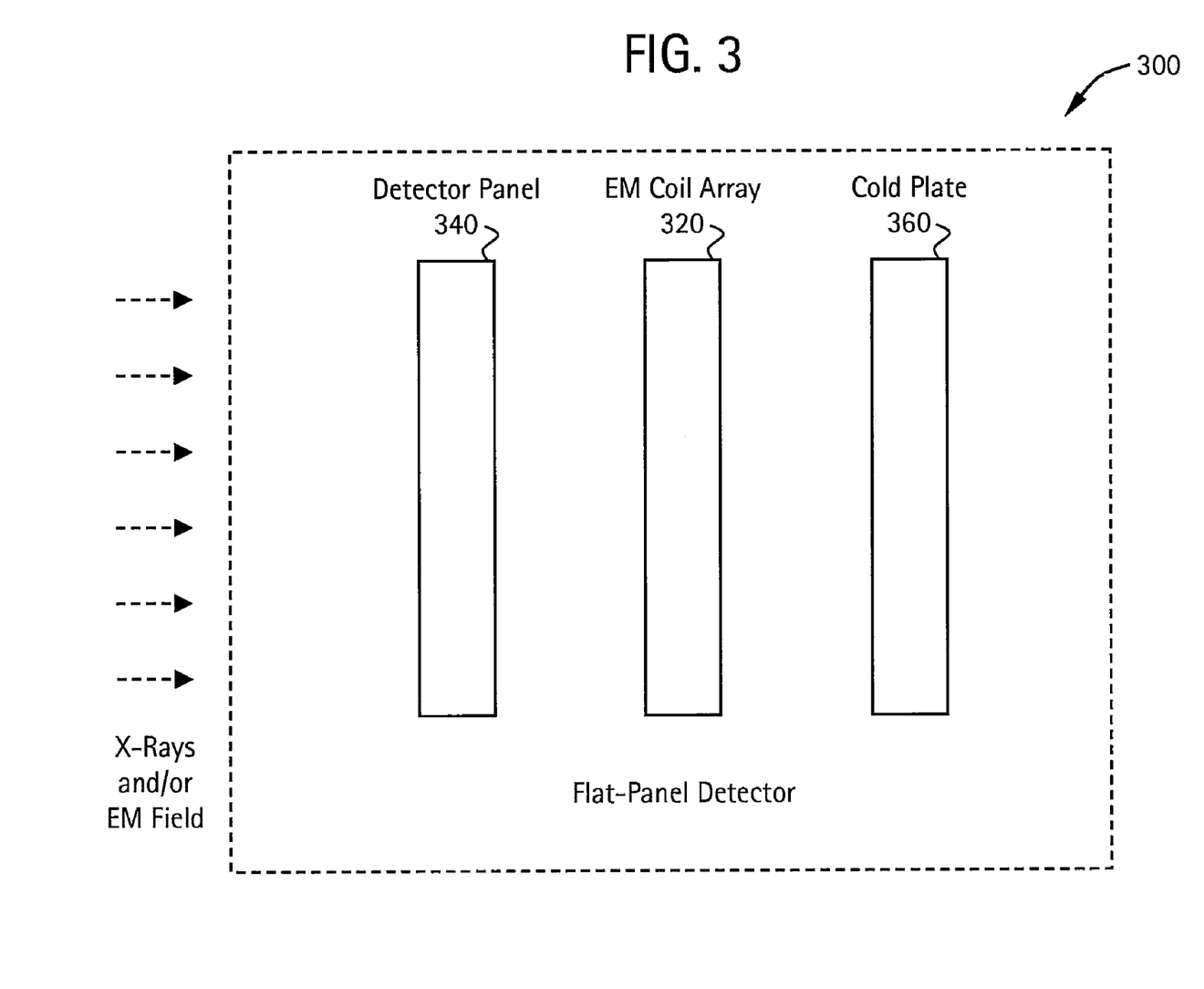
FIG. 3 illustrates a cross-sectional view of a flat-panel detector with an electromagnetic coil array in accordance with an embodiment of the present invention.

In an embodiment, the detector 140 may include a flat-panel detector, such as the flat-panel detector 300 of FIG. 3.

Figure 4:
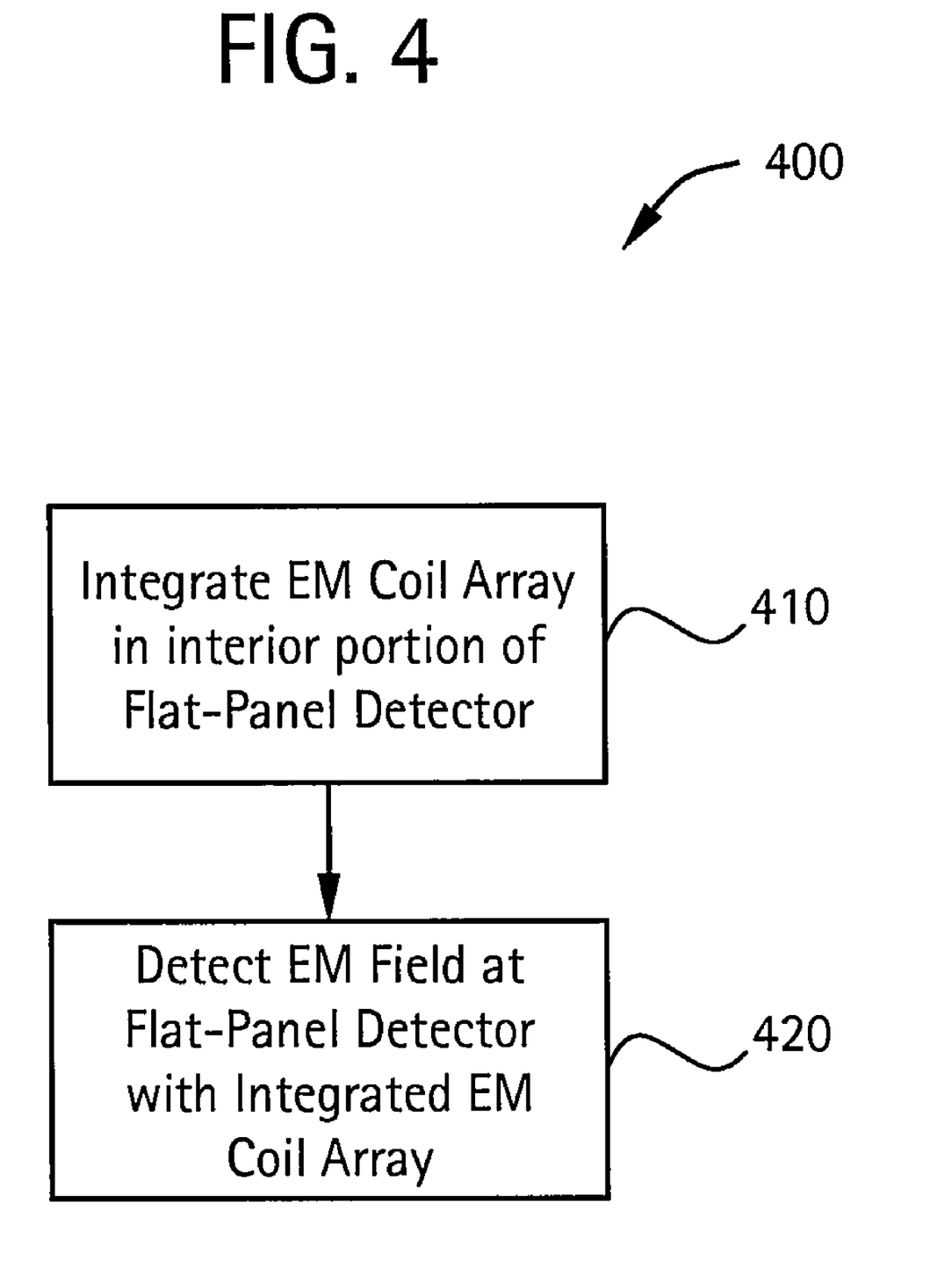
FIG. 4 illustrates a flow diagram of a method for detecting an electromagnetic field with a flat-panel detector in accordance with an embodiment of the present invention.

In an embodiment, the imaging system 100 may also include an antiscatter grid 180, such as the antiscatter grid 400 of FIG. 4. The antiscatter grid 180 may be positioned between the x-ray detector 140 and the object 160. As described above, the x-rays may travel from the x-ray source 120, through the object 160, and to the x-ray detector 140. The x-rays may be incident x-rays and/or scattered x-rays. The scattered x-rays may result from the presence of the object 160. The antiscatter grid 180 may filter the scattered x-rays from the object 160, while allowing the incident x-rays to pass through to the x-ray detector 140. As appreciated by one of ordinary skill in the art, the difference between scattered x-rays, which are filtered, and incident x-rays, which are not filtered, may be a function of the particular antiscatter grid selected.

In an embodiment, the imaging system 100 may be implemented in conjunction with a tracking system, as described below.

Figure 2:
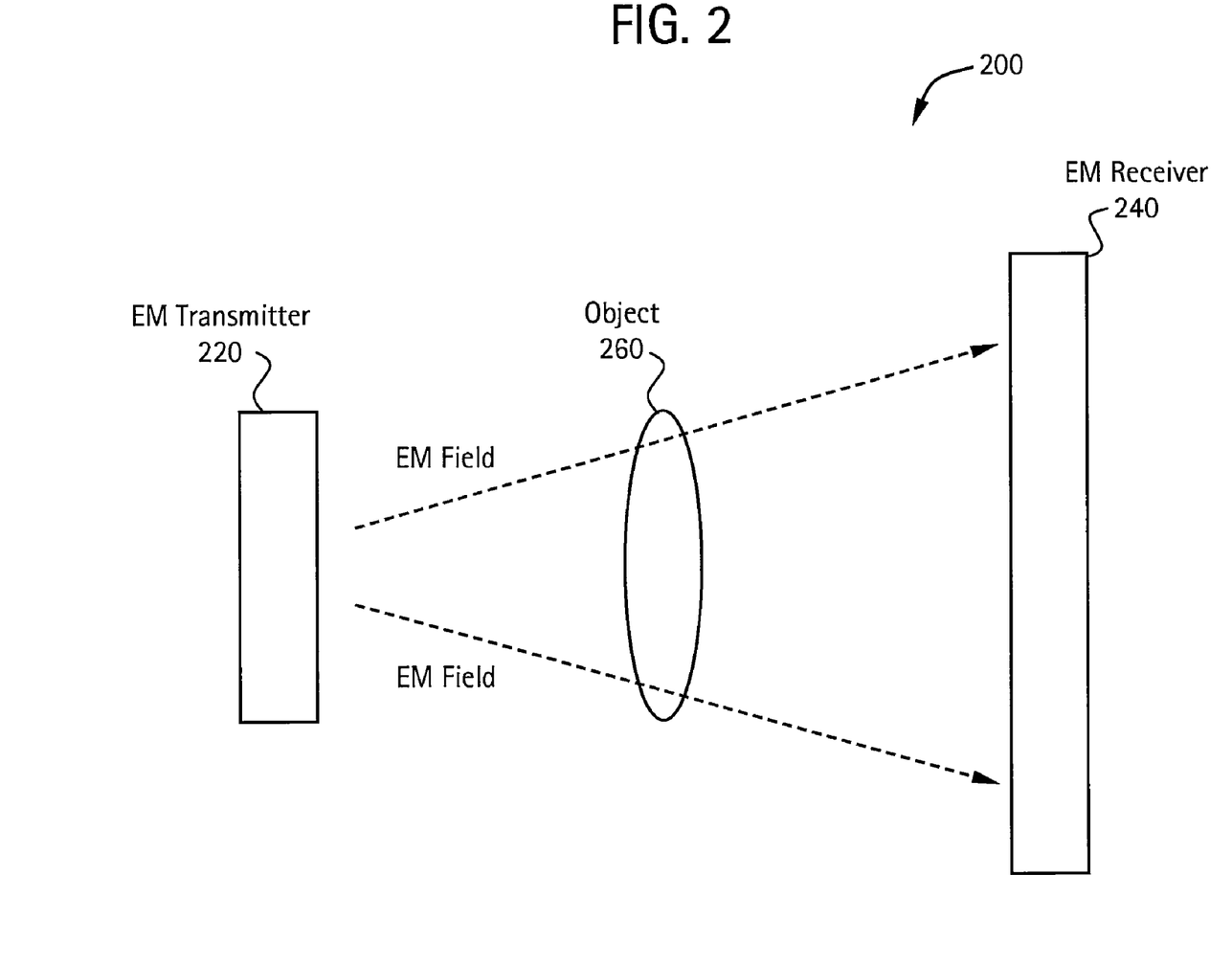
FIG. 2 illustrates a tracking system in accordance with an embodiment of the present invention.

FIG. 2 illustrates a tracking system 200 in accordance with an embodiment of the present invention. For purposes of illustration only, the tracking system 200 is described as an electromagnetic tracking system. As appreciated by one of ordinary skill in the art, other tracking systems may be similarly implemented. The tracking system 200 includes an electromagnetic transmitter 220 and an electromagnetic receiver 240. An object 260 may also be present in the tracking system 200.

In an embodiment, the electromagnetic transmitter 210 may transmit an electromagnetic field. The electromagnetic field may be an incident electromagnetic field and/or a scattered electromagnetic field. The scattered electromagnetic field may result from the presence of the an object, such as the object 160 of FIG. 1, being imaged by an imaging system, such as the imaging system 100. The electromagnetic receiver 240 may receive the electromagnetic field.

In an embodiment, the electromagnetic transmitter 220 and/or the electromagnetic receiver 240 may include an electromagnetic coil array. The electromagnetic coil array may include one or more electromagnetic coils. In an embodiment, the electromagnetic coil array may be integrated into a flat-panel detector, such as the flat-panel detector 120 of FIG. 1, as described below with respect to the flat-panel detector 300 of FIG. 3. In an embodiment, the electromagnetic coil array may be integrated into an antiscatter grid, such as the antiscatter grid 160 of FIG. 1, as described below with respect to the antiscatter grid 400 of FIG. 4.

In an embodiment, the tracking system 200 may include one or more electromagnetic transmitters 220 and/or one or more electromagnetic receivers 240. In an embodiment, the tracking system 200 may include an electromagnetic transceiver 260 (not shown). The electromagnetic transceiver 260 may perform the functions of the electromagnetic transmitter 220 and/or the electromagnetic receiver 240. That is, the electromagnetic transceiver 260 may transmit and/or receive an electromagnetic field. In an embodiment, the electromagnetic transceiver 260 may replace the electromagnetic transmitter 260 and/or the electromagnetic receiver 240 in the electromagnetic tracking system 200.

FIG. 3 illustrates a cross-sectional view of a flat-panel detector 300 with an electromagnetic coil array 320 in accordance with an embodiment of the present invention. The flat-panel detector 300 includes the electromagnetic coil array 320. In an embodiment, the flat-panel detector 300 may include a detector panel 340 and a cold plate 360. As appreciated by one of ordinary skill in the art, the flat-panel detector 300 may include other components, such as scintillators, light pipes, beam stops, and/or readout electronics. In an embodiment, the flat-panel detector 300 may be an amorphous silicon flat-panel detector, for example.

In an embodiment, the electromagnetic coil array 320 may be an electromagnetic transmitter, such as the electromagnetic transmitter 220 of FIG. 2. In an embodiment, the electromagnetic coil array 320 may be an electromagnetic receiver, such as the electromagnetic receiver 240 of FIG. 2. In an embodiment, the electromagnetic coil array 320 may be an electromagnetic transceiver, such as the electromagnetic transceiver 260 of FIG. 2.

In an embodiment, the electromagnetic coil array 320 may include one or more electromagnetic coils. In an embodiment, the electromagnetic coil array 320 may be a printed circuit board (PCB) electromagnetic coil array, such as the PCB electromagnetic coil array 900 of FIG. 9. The PCB electromagnetic coil array may be thin enough to fit within the flat-panel detector. As described below, rigid PCBs or rigid circuits may be as thin as about 1 mm to about 2 mm, for example, whereas flexible PCBs or flex circuits may be as thin as 0.1 mm to about 0.2 mm, for example.

In an embodiment, the detector panel 340 may include a plurality of detector elements, such as photodiodes. In an embodiment, the detector panel 340 may include glass, for example. In an embodiment, the detector panel 340 may include non-conductive components, such as non-conductive coatings. In an embodiment, the detector panel 340 may include partially conductive components, such as partially conductive coatings. In an embodiment, the detector panel 340 may not include any highly conductive components.

In an embodiment, the cold plate 340 may include metal, such as stainless steel and/or aluminum. In an embodiment, the cold plate 340 may include one or more coolant channels. For example, water, ethylene glycol, and/or other coolant may be pumped through the cooling channels in the cold plate 340 to cool the flat-panel detector 300.

In an embodiment, the electromagnetic coil array 320 may be positioned inside of the flat-panel detector 300. In an embodiment, the electromagnetic coil array 320 may be positioned behind the detector panel 340 in the flat-panel detector 300. More particularly, the electromagnetic coil array 320 may be positioned behind the field of view of the detector panel 340, for example, with respect to an x-ray source, such as the x-ray source 120 of FIG. 1. In an embodiment, the electromagnetic coil array 320 may be positioned between the detector panel 340 and the cold plate 360 in the flat-panel detector 300.

In an embodiment, the detector panel 340 may be transparent to electromagnetic fields. More particularly, the detector panel 340 may be transparent to electromagnetic fields because the detector panel may not include any highly conductive materials, as described above. The detector panel 340 may be transparent to electromagnetic fields with frequencies less than about 40 kHz, for example. The detector panel 340 may be transparent to electromagnetic fields with frequencies less than about 1 GHz, for example. The detector panel 340 may be transparent to electromagnetic fields with frequencies that are also transparent to the human body, for example. Consequently, the operation of the electromagnetic coil array 320 may not interfere with operation of the flat-panel detector 300.

In an embodiment, the electromagnetic fields may be alternating current (AC) and/or pulsed direct current (PDC), for example.

FIG. 4 illustrates a flow diagram of a method 400 for detecting an electromagnetic field with a flat-panel detector in accordance with and embodiment of the present invention. The method 400 includes integrating an electromagnetic coil array in an interior portion of the flat-panel detector 410 and detecting the electromagnetic field at the flat-panel detector with the integrated electromagnetic coil array 420.

At step 410, the electromagnetic coil array may be integrated in an interior portion of the flat-panel detector, as described above.

At step 420, the electromagnetic field at the flat-panel detector may be detected with the integrated electromagnetic coil array, as described above.

As will be appreciated by those of skill in the art, certain steps may be performed in ways other than those recited above and the steps may be performed in sequences other than those recited above.

Figure 5:
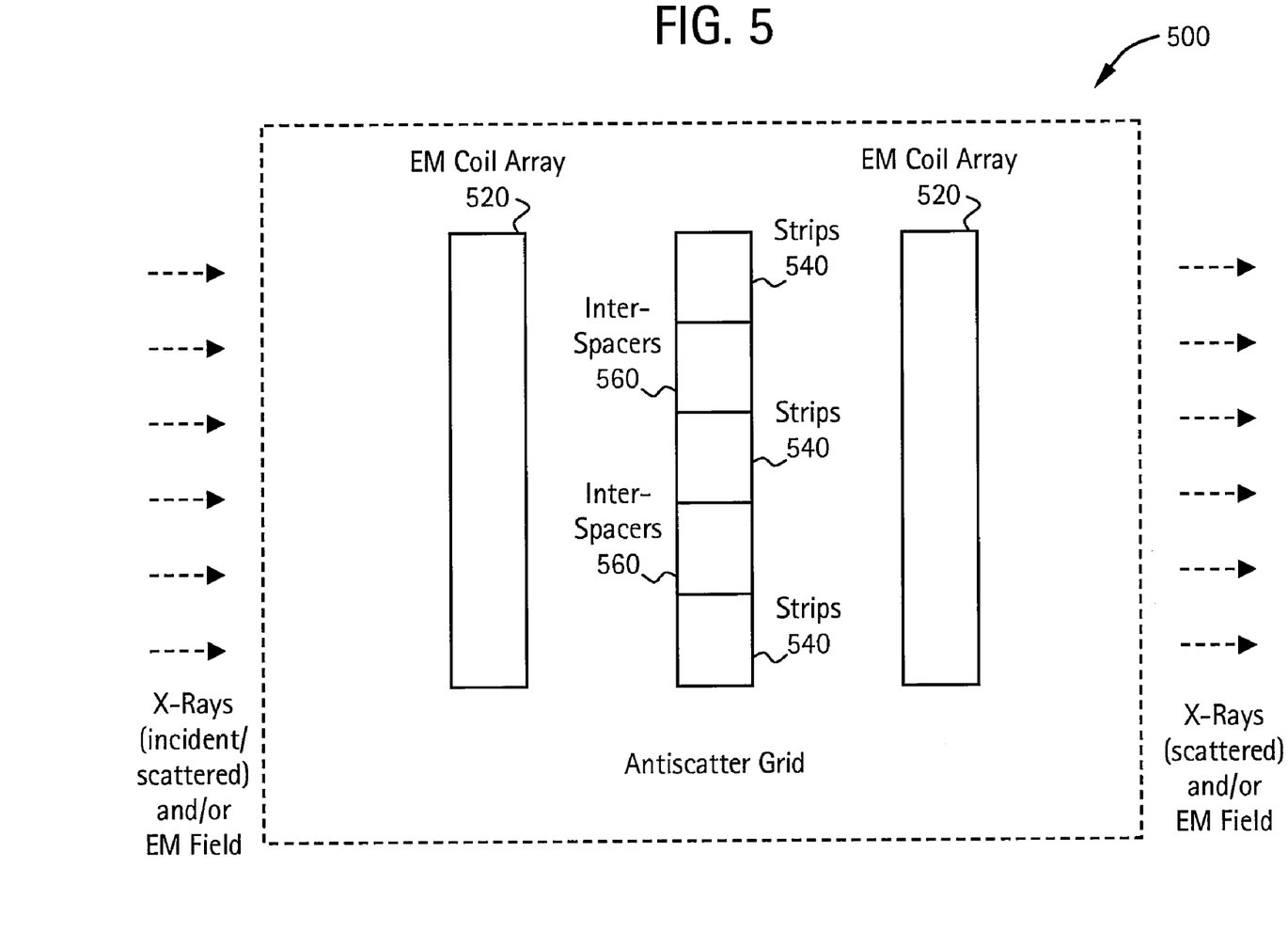
FIG. 5 illustrates a cross-sectional view of an antiscatter grid with an electromagnetic coil array in accordance with an embodiment of the present invention.

FIG. 5 illustrates a cross-sectional view of an antiscatter grid 500 with an electromagnetic coil array 520 in accordance with an embodiment of the present invention. The antiscatter grid 500 includes the electromagnetic coil array 520. In an embodiment, the antiscatter grid 500 may include one or more strips 540 and one or more interspacers 560. As appreciated by one of ordinary skill in the art, the antiscatter grid 500 may include other components. In an embodiment, the antiscatter grid 500 may be an x-ray antiscatter grid, such as the antiscatter grid 160 of FIG. 1.

In an embodiment, the electromagnetic coil array 520 may be an electromagnetic transmitter, such as the electromagnetic transmitter 220 of FIG. 2. In an embodiment, the electromagnetic coil array 520 may be an electromagnetic receiver, such as the electromagnetic receiver 240 of FIG. 2. In an embodiment, the electromagnetic coil array 520 may be an electromagnetic transceiver, such as the electromagnetic transceiver 260 of FIG. 2.

In an embodiment, the electromagnetic coil array 520 may include one or more electromagnetic coils. In an embodiment, the electromagnetic coil array 520 may be a printed circuit board (PCB) electromagnetic coil array, such as the PCB electromagnetic coil array 900 of FIG. 9.

In an embodiment, the strips 540 may include x-ray opaque materials, such as lead. In an embodiment, the interspaces 560 may include x-ray transparent materials, such as aluminum. In an embodiment, the antiscatter grid 500 may be a strip grid, for example. That is, the strips 540 may be positioned to form a grid that is substantially parallel in orientation and either substantially horizontal or substantially vertical in direction. In an embodiment, the antiscatter grid 500 may be cross grid, for example. That is, the strips 540 may be positioned to form a grid that is substantially parallel in orientation and both substantially horizontal and substantially vertical in direction. In an embodiment, the interspacers 560 may be positioned between the strips 540. In an embodiment, the antiscatter grid 500 may be an antiscatter grid available from Soyee Products, Incorporated (Danielson, Conn.).

In an embodiment, the electromagnetic coil array 520 may be positioned in front of the antiscatter grid 500. More particularly, the electromagnetic coil array 520 may be positioned in front of the field of view of the antiscatter grid 500, for example, with respect to an x-ray source, such as the x-ray source 120 of FIG. 1.

In an embodiment, the electromagnetic coil array 520 may be positioned behind the antiscatter grid 500. More particularly, the electromagnetic coil array 520 may be positioned behind the field of view of the antiscatter grid 500, for example, with respect to an x-ray source, such as the x-ray source 120 of FIG. 1.

In an embodiment, the electromagnetic coil array 520 may be attached to the antiscatter grid 500.

In an embodiment, the electromagnetic coil array 520 may be registered with the antiscatter grid 500. That is, the electromagnetic coil array 500 may be positioned such that the operation of the electromagnetic coil array 520 does not interfere with the operation of the antiscatter grid 500. In other words, incident x-rays allowed to pass through the antiscatter grid 500 may also pass through the electromagnetic coil array 520. Conversely, scattered x-rays filtered or blocked by the antiscatter grid 500 may also be filtered or blocked by the electromagnetic coil array 520.

Figure 6:
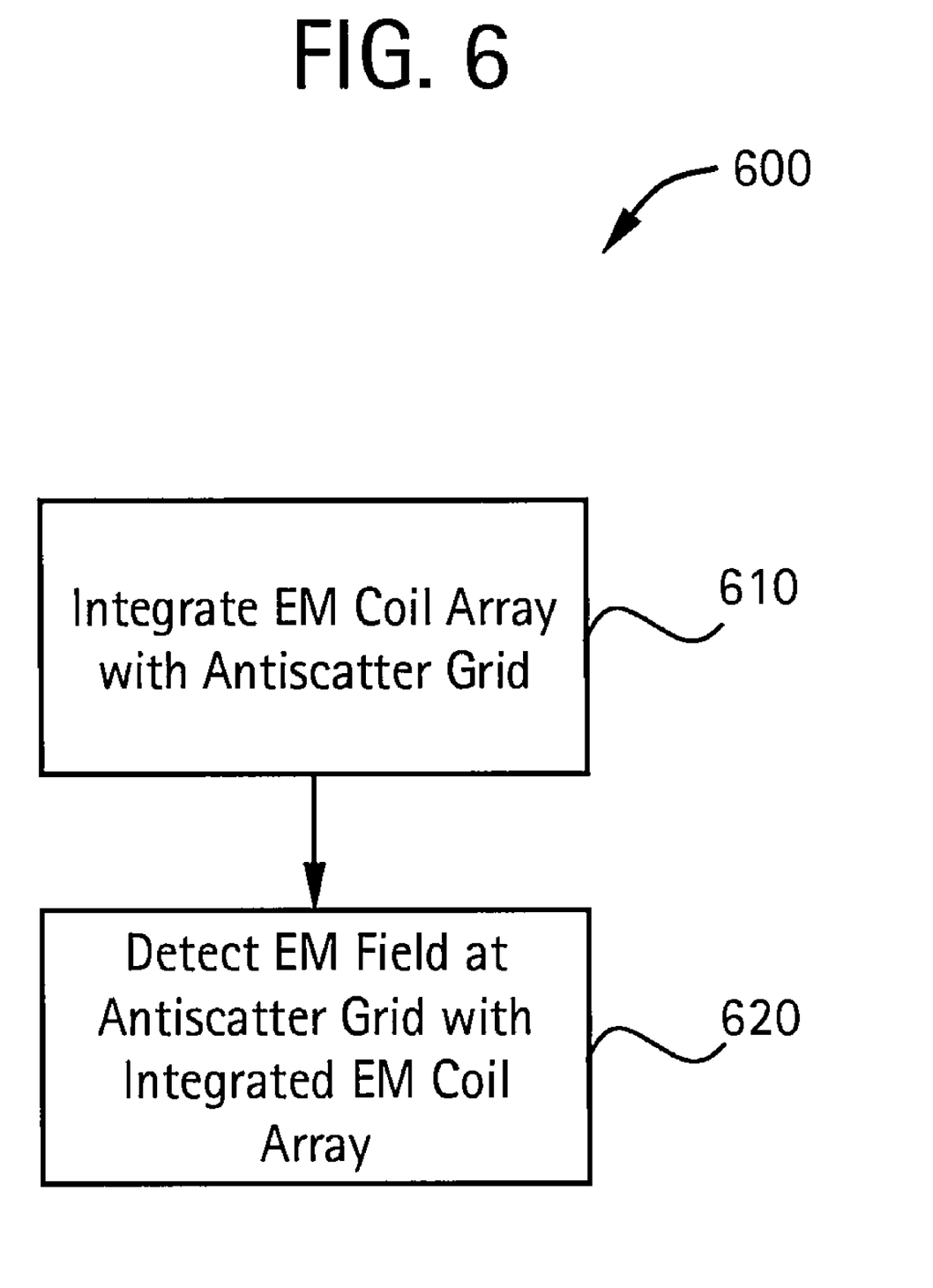
FIG. 6 illustrates a flow diagram of a method for detecting an electromagnetic field with an antiscatter grid in accordance with an embodiment of the present invention.

FIG. 6 illustrates a flow diagram of a method 600 for detecting an electromagnetic field with an antiscatter grid in accordance with and embodiment of the present invention. The method includes integrating an electromagnetic coil array with an antiscatter grid 610 and detecting the electromagnetic field at the antiscatter grid with the integrated electromagnetic coil array 620. The electromagnetic coil array may be registered with the antiscatter grid.

At step 610, the electromagnetic coil array may be integrated with the antiscatter grid, as described above.

At step 620, the electromagnetic field at the antiscatter grid may be detected with the integrated electromagnetic coil array, as described above.

As will be appreciated by those of skill in the art, certain steps may be performed in ways other than those recited above and the steps may be performed in sequences other than those recited above.

Figure 7:
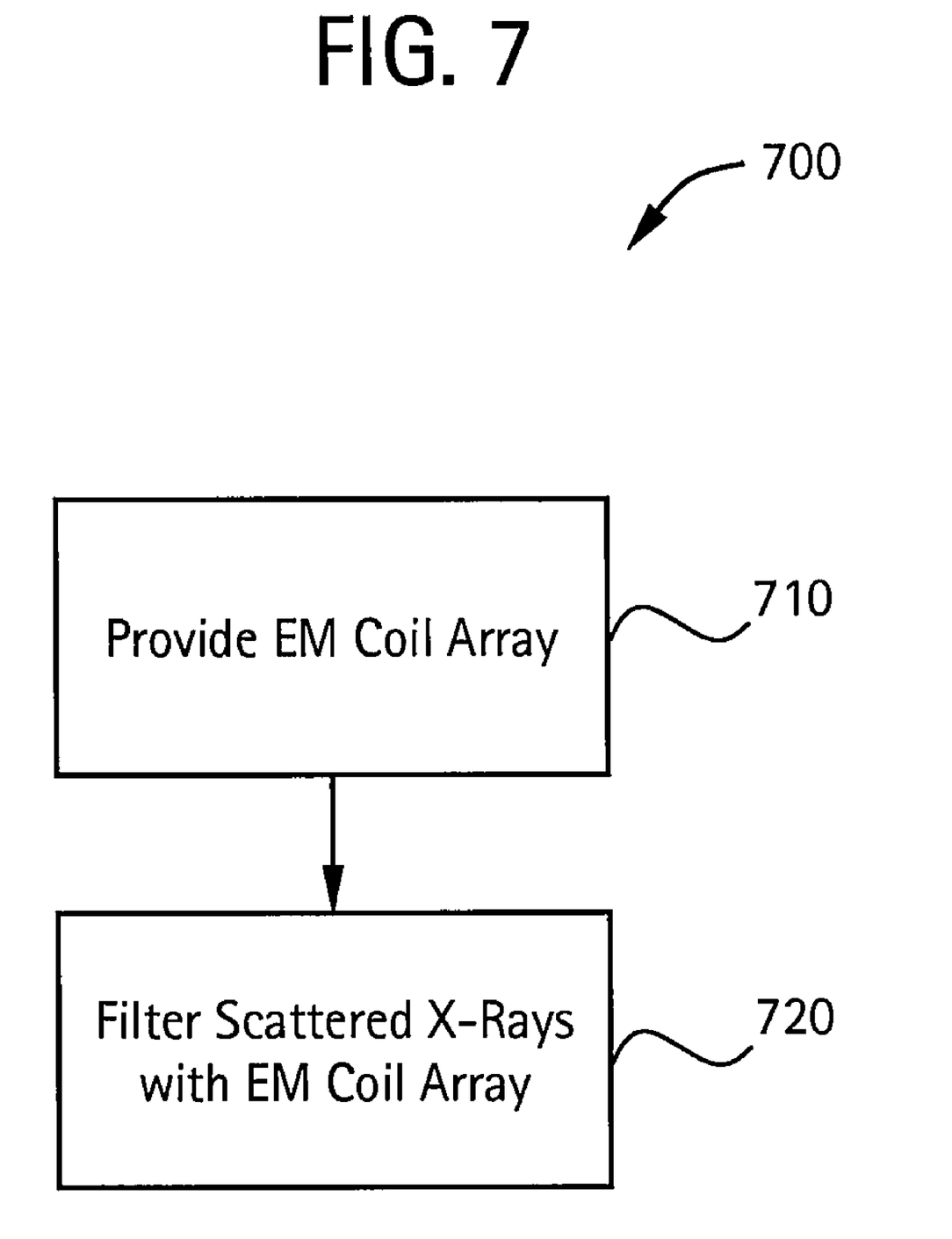
FIG. 7 illustrates a flow diagram of a method for using an electromagnetic coil array as an antiscatter grid in accordance with an embodiment of the present invention.

FIG. 7 illustrates a flow diagram of a method 700 for using an electromagnetic coil array as an antiscatter grid in accordance with an embodiment of the present invention. The method 700 includes providing the electromagnetic coil array and filtering scattered x-rays with the electromagnetic coil array.

At step 710, an electromagnetic coil array may be provided. The electromagnetic coil array may be the electromagnetic coil array 500 of FIG. 5. The electromagnetic coil array may be a printed circuit board (PCB) electromagnetic coil array, such as the PCB electromagnetic coil array 900 of FIG. 9. The PCB electromagnetic coil array may include a substrate, such as the substrate 940 of FIG. 9, and one or more tracks, such as the tracks 560 of FIG. 9. The substrate may be transparent to x-rays. The tracks may be opaque to x-rays.

At step 720, scattered x-rays may be filtered by the electromagnetic coil array, while incident x-rays may pass through the electromagnetic coil array. That is, the electromagnetic coil array may function as the antiscatter grid, such as the antiscatter grid 180 of FIG. 1 or the antiscatter grid 500 of FIG. 5.

As will be appreciated by those of skill in the art, certain steps may be performed in ways other than those recited above and the steps may be performed in sequences other than those recited above.

Figure 8:
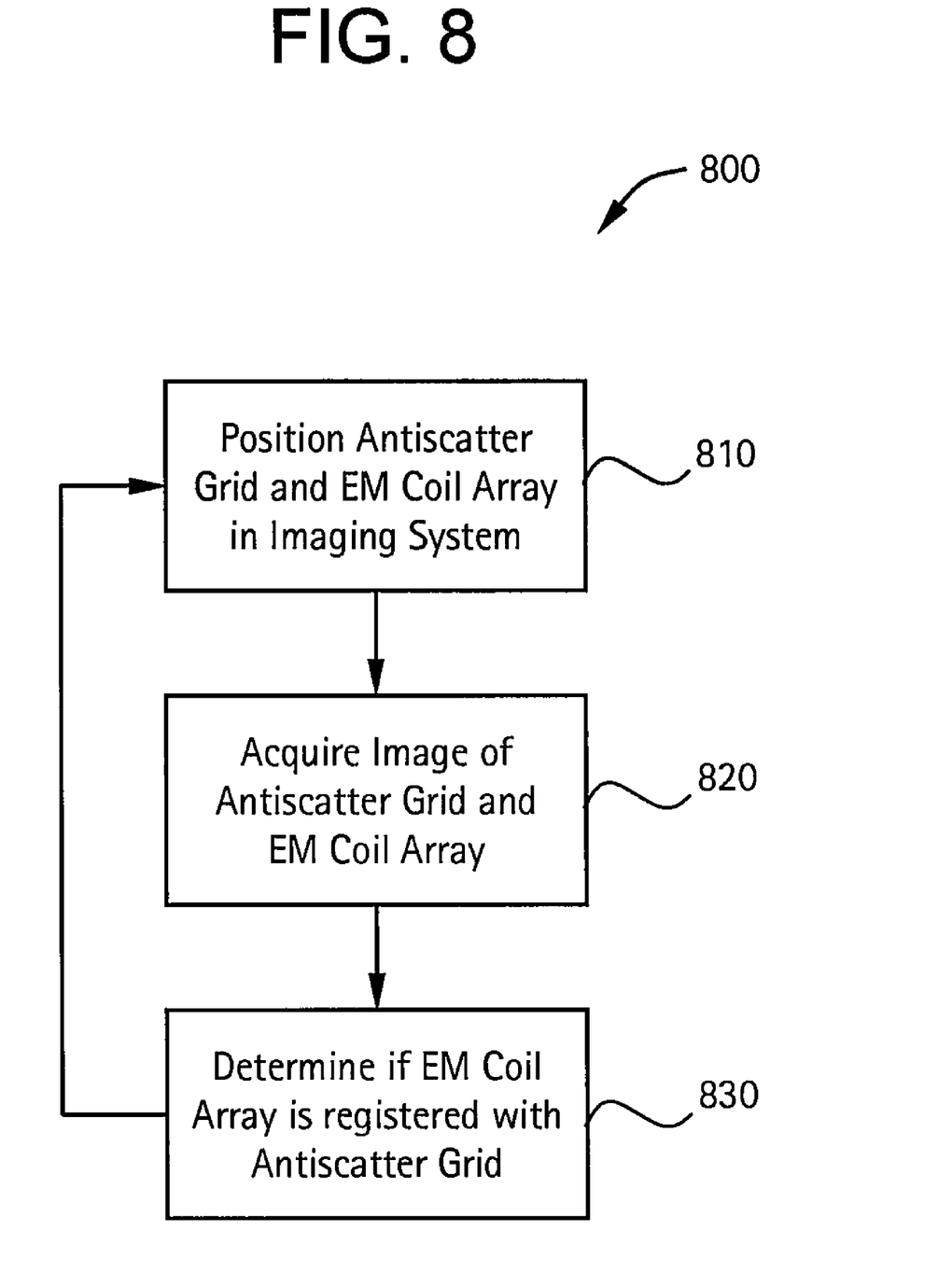
FIG. 8 illustrates a flow diagram of a method for registering an electromagnetic coil array with an antiscatter grid in accordance with an embodiment of the present invention.

FIG. 8 illustrates a flow diagram of a method 800 for registering an electromagnetic coil array with an antiscatter grid in accordance with an embodiment of the present invention. The method 800 includes positioning the antiscatter grid and the electromagnetic coil array in the imaging system 810, acquiring an image of the antiscatter grid and the electromagnetic coil array 820, and determining that the electromagnetic coil array is registered with the antiscatter grid based at least in part on the acquired image 830. In an embodiment, the method 800 may also include repositioning the antiscatter grid and/or the electromagnetic coil array in the imaging system 840.

At step 810, the antiscatter grid and the electromagnetic coil array may be positioned in the imaging system. The antiscatter grid may be the antiscatter grid 160 of FIG. 1 or the antiscatter grid 500 of FIG. 5. The electromagnetic coil array may be the electromagnetic coil array 520 of FIG. 5 or the printed circuit board (PCB) electromagnetic coil array 900 of FIG. 9. The imaging system may be the imaging system 100 of FIG. 1. As described above, the antiscatter grid may be positioned independent of the electromagnetic coil array. Conversely, the electromagnetic coil array may be attached to the antiscatter grid.

At step 820, an image of the antiscatter grid and the electromagnetic coil array may be acquired. More particularly, the image of the antiscatter grid and the electromagnetic coil array may be acquired by the imaging system, such as the imaging system 100 of FIG. 1. The antiscatter grid and the electromagnetic coil array may be an object, such as the object 160 of FIG. 1.

At step 830, a determination that the electromagnetic coil array is registered with the antiscatter grid may be based at least in part on the acquired image of the antiscatter grid and the electromagnetic coil array. In a low resolution image, for example, a moire patterns may be visible when the electromagnetic coil array is not registered with the antiscatter grid. In a high resolution image, the electromagnetic coil array may be visible when the electromagnetic coil array is not registered with the antiscatter grid.

At step 840, the antiscatter grid and/or the electromagnetic coil array may be repositioned in the imaging system. More particularly, if the electromagnetic coil array is not registered with the antiscatter grid, then the antiscatter grid and/or the electromagnetic coil array may be repositioned in the imaging system. The steps 820-840 of the method 800 may be repeated as necessary until the electromagnetic coil array is registered with the antiscatter grid.

As will be appreciated by those of skill in the art, certain steps may be performed in ways other than those recited above and the steps may be performed in sequences other than those recited above.

Figure 9:
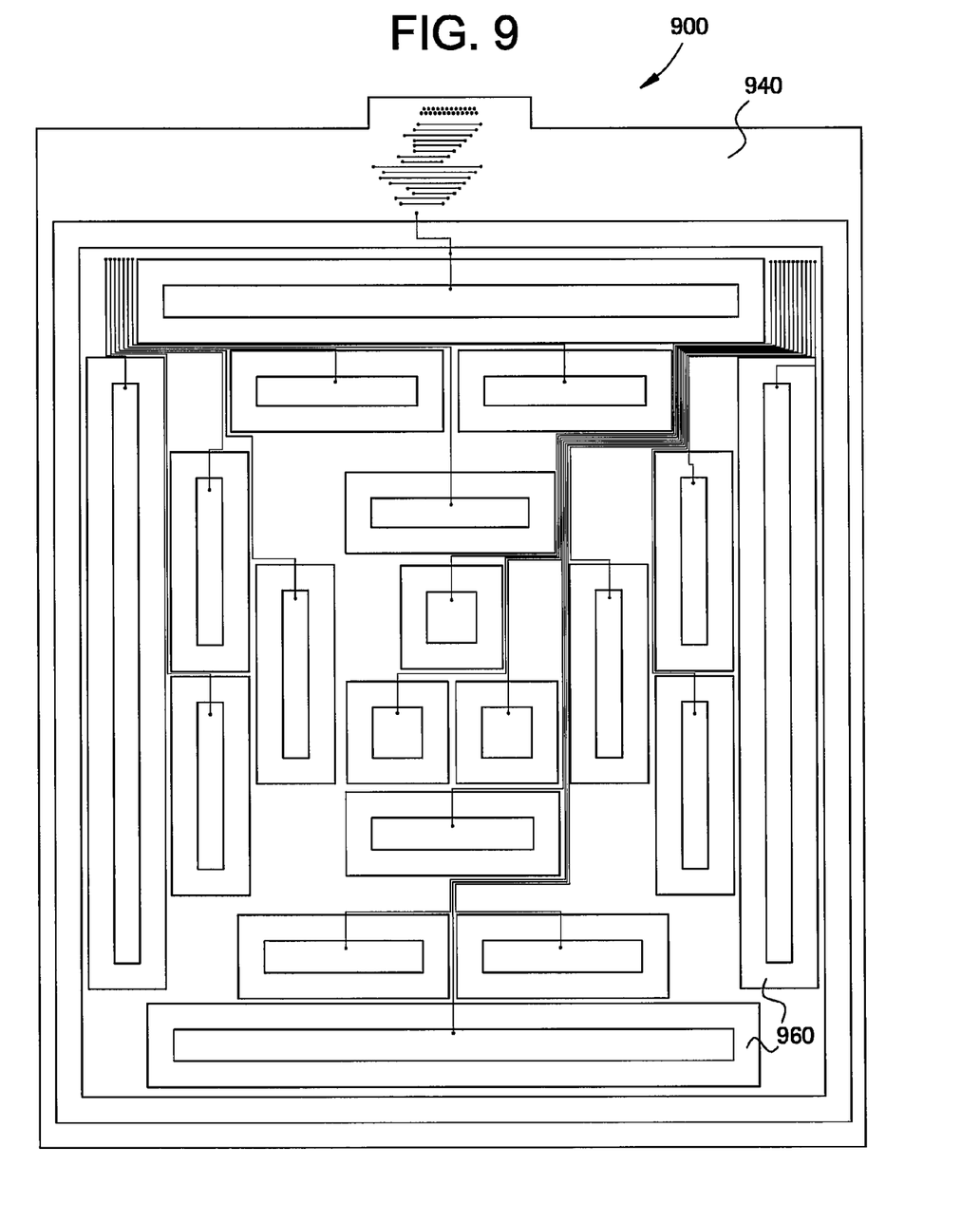
FIG. 9 illustrates a plan view of a printed circuit board electromagnetic coil array in accordance with an embodiment of the present invention.

FIG. 9 illustrates a plan view of a printed circuit board (PCB) electromagnetic coil array 900 in accordance with an embodiment of the present invention. The PCB electromagnetic coil array 900 includes a substrate 940 and one or more tracks 960. As appreciated by one of ordinary skill in the art, the PCB electromagnetic coil array 900 may include other PCB components. Anderson (U.S. patent application Ser. No. 11/611,112), herein incorporated by reference, provides an example of the PCB electromagnetic coil array 900.

In an embodiment, the substrate 940 may include rigid materials, such as epoxy-fiberglass composites (i.e., fiberglass in an epoxy resin binder) and/or other rigid materials. For example, the substrate 940 may include G-10 and/or FR-4, both of which are available from Rogers Corporation (Rogers, Conn.).

In an embodiment, the substrate 940 may include flexible materials, such as polymer films and/or other flexible materials. For example, the substrate 940 may include polyester films, such as Mylar®, and/or polyamide films, such as Kapton®, both available from DuPont (Circleville, Ohio). Printed circuit boards made with completely flexible and partially flexible substrates are commonly referred to as a flex circuits and rigid-flex circuits, respectively.

In an embodiment, the substrate 940 may include (electrically) non-conductive materials. For example, all of the rigid and flexible substrate materials may also be (electrically) non-conductive.

In an embodiment, the tracks 960 may include (electrically) conductive materials, such as copper, aluminum, gold and/or silver. Gold and/or silver tracks may be more expensive and more difficult to process than other (electrically) conductive materials.

In an embodiment, the tracks 960 may include spirals, such as square, rectangle, circle, triangle, and/or other shaped spirals.

In an embodiment, the tracks 960 of the PCB electromagnetic coil array 900 may form one or more electromagnetic coils.

In an embodiment, the tracks 960 may be attached to the substrate 940, for example, by a photolithographic process, a microwire process, and/or a handwire process. In a subtraction process, for example, copper foil may be glued to a substrate 940 and then etched to form copper tracks 960. In an addition process, for example, aluminum may be sputtered onto a substrate 940 in a vacuum chamber to form aluminum tracks 960. In another addition process, for example, glue may be applied to the substrate 940 and then wire may be attached to the substrate 940 with the glue to form the tracks 960.

As described above, the PCB electromagnetic coil array 900 may be integrated into a flat-panel detector, such as the flat-panel detector 300 of FIG. 3.

As described above, the PCB electromagnetic coil array 900 may be integrated into an antiscatter grid, such as the antiscatter grid 400 of FIG. 4. In an embodiment, the substrate 940 may be an x-ray transparent substrate. The x-ray transparent characteristics of the substrate 940 may depend on the substrate material. For example, all of the rigid, flexible, and (electrically) non-conductive substrate materials may also be x-ray transparent. The x-ray transparent characteristics of the substrate 940 may depend on the substrate thickness. The substrate 940 may be x-ray transparent at thicknesses less than about 2 mm. The substrate 940 may be x-ray transparent at thicknesses less than 1 mm.

As described above, the PCB electromagnetic coil array 900 may be registered with an antiscatter grid, such as the antiscatter grid 400 of FIG. 4. More particularly, the substrate 940 of the PCB electromagnetic coil array 900 may be registered with the interspacers 460 of the antiscatter grid 400. That is, incident x-rays allowed to pass through the interspacers 460 may also pass through the substrate 940. Additionally, the tracks 960 of the PCB electromagnetic coil array 900 may be registered with the strips 440 of the antiscatter grid 400. That is, scattered x-rays filtered by the strips 440 may also be filtered by the tracks 960. In other words, the substrate 940 and the tracks 960 may be positioned such that the operation of the PCB electromagnetic coil array 900 does not interfere with the operation of the antiscatter grid 400.

An imaging system, such as the imaging system 100 of FIG. 1, may be utilized to determine if the electromagnetic coil array 420 is registered with the antiscatter grid 400. In an embodiment of the present invention, the antiscatter grid 400 may be visible with a high resolution imaging system. If the electromagnetic coil array 420 is not visible when introduced into the high resolution imaging system, then the electromagnetic coil array 420 is registered with the antiscatter grid 400. Conversely, if the electromagnetic coil array 420 is not visible when introduced into the imaging system, then the electromagnetic coil array may not be registered with the antiscatter grid 400.

Yatsenko et al. (U.S. patent application Ser. No. 11/271,604), herein incorporated by reference, provides a system and method for integration of a calibration target into a c-arm. More particularly, Yatsenko et al. teaches intrinsic geometry calibration using moire patterns produced by existing x-ray system components. If the antiscatter grid is used to locate the x-ray source in the x-ray image coordinates, the tracker coil array may be inherently pre-registered to the x-ray image, and thus, the tracker coordinates may be registered with the image coordinates.

In an embodiment, the PCB electromagnetic coil array 900 may function as an antiscatter grid, such as the antiscatter grid 400 of FIG. 4. That is, incident x-rays may pass through the substrate 940, while scattered x-rays may be filtered by the tracks 960. As described above, the substrate 940 may be x-ray transparent, thus allowing incident x-rays to pass through the PCB electromagnetic coil array 900. The tracks 960 may be x-ray opaque, thus filtering scattered x-rays. More particularly, the x-ray opaque properties of the tracks 960 may depend on the track material and/or the track thickness. For example, lead tracks greater than about 1 mm in thickness may be sufficient to filter scattered x-rays, and thus, allow the PCB electromagnetic coil array 900 to function as an antiscatter grid.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. An antiscatter grid including an electromagnetic coil array integrated with the antiscatter grid, wherein the electromagnetic coil array is registered with the antiscatter grid and wherein the electromagnetic coil array is configured to detect an electromagnetic field at the antiscatter grid.

2. The antiscatter grid of claim 1, wherein the electromagnetic coil array is in front of the antiscatter grid.

3. The antiscatter grid of claim 1, wherein the electromagnetic coil array is behind the antiscatter grid.

4. The antiscatter grid of claim 1, wherein the electromagnetic coil array is attached to the antiscatter grid.

5. The antiscatter grid of claim 1, wherein a portion of the electromagnetic coil array is transparent to x-rays.

6. The antiscatter grid of claim 1, wherein the electromagnetic coil array is a printed circuit board (PCB) electromagnetic coil array.

7. The antiscatter grid of claim 6, wherein the PCB electromagnetic coil array includes at least one electromagnetic coil.

8. The antiscatter grid of claim 6, wherein the PCB electromagnetic coil array includes a substrate and wherein the substrate is transparent to x-rays.

9. The antiscatter grid of claim 1, wherein the electromagnetic coil array is an electromagnetic receiver.

10. The antiscatter grid of claim 1, wherein the electromagnetic coil array is an electromagnetic transmitter.

11. The antiscatter grid of claim 1, wherein the electromagnetic coil array is an electromagnetic transceiver.

12. The antiscatter grid of claim 1, wherein the electromagnetic coil array includes at least one electromagnetic coil.

13. A method for detecting an electromagnetic field with an antiscatter grid, the method including:
   integrating an electromagnetic coil array with an antiscatter grid; and
   detecting the electromagnetic field at the antiscatter grid with the integrated electromagnetic coil array, wherein the electromagnetic coil array is registered with the antiscatter grid.

14. The method of claim 13, wherein the electromagnetic coil array is in the field of view of the antiscatter grid.

15. The method of claim 13, wherein the electromagnetic coil array is a printed circuit board (PCB) electromagnetic coil array.

16. The method of claim 15, wherein the PCB electromagnetic coil array includes at least one electromagnetic coil.

17. The method of claim 13, wherein the electromagnetic coil array is an electromagnetic receiver.

18. The method of claim 13, wherein the electromagnetic coil array is an electromagnetic transceiver.

19. A method for using an electromagnetic coil array as an antiscatter grid, the method including:
   providing the electromagnetic coil array, wherein said electromagnetic coil array is printed circuit board (PCB)

electromagnetic coil array with at least one track of said electromagnetic coil array etched into a PCB substrate material; and filtering scattered x-rays with the electromagnetic coil array.

20. The method of claim 19, wherein the PCB electromagnetic coil array includes a substrate and at least one track, wherein the substrate is transparent to x-rays, and wherein the at least one track is opaque to x-rays.

21. A method for registering an electromagnetic coil array integrated with an antiscatter grid, the method including:

positioning the antiscatter grid and the integrated electromagnetic coil array in an imaging system;

acquiring an image of the antiscatter grid and the electromagnetic coil array; and determining that the electromagnetic coil array is registered with the antiscatter grid based at least in part on the image of the antiscatter grid and the electromagnetic coil array.

22. The method of claim 21, further including repositioning the antiscatter grid and the electromagnetic coil array in the imaging system.

23. The method of claim 21, wherein the determining step is based at least in part on the presence of a moire pattern in the acquired image.

24. The method of claim 21, wherein the determining step is based at least in part on the visibility of the electromagnetic coil array.

25. A printed circuit board (PCB) electromagnetic coil array integrated with an antiscatter grid, the PCB electromagnetic coil array configured to detect an electromagnetic field at the antiscatter grid.

26. A printed circuit board (PCB) electromagnetic coil array configured to function as an antiscatter grid wherein the PCB electromagnetic coil array includes a substrate and at least one track, wherein at least one track etched into the substrate PCB material.

* * * * *